(12) United States Patent
Bedford

(10) Patent No.: US 7,051,455 B2
(45) Date of Patent: May 30, 2006

(54) CHEMICAL COMPOSITIONS AND METHODS FOR ABSORBING WATER VAPOR AND COMBATING MALODOR WITHIN A CAVITY

(75) Inventor: David Bedford, Hull (GB)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 10/502,484

(22) PCT Filed: Jan. 29, 2003

(86) PCT No.: PCT/GB03/00352

§ 371 (c)(1),
(2), (4) Date: Dec. 9, 2004

(87) PCT Pub. No.: WO03/063918

PCT Pub. Date: Aug. 7, 2003

(65) Prior Publication Data

US 2005/0115844 A1 Jun. 2, 2005

(30) Foreign Application Priority Data

Jan. 30, 2002 (GB) .................. 0202059.2

(51) Int. Cl.
*F26B 5/04* (2006.01)
(52) U.S. Cl. ...................................... 34/416
(58) Field of Classification Search .................. 34/416, 34/80, 90, 106
See application file for complete search history.

(56) References Cited

U.S. PATENT DOCUMENTS

| | | | | |
|---|---|---|---|---|
| 5,261,169 A | * | 11/1993 | Williford | 36/43 |
| 5,542,191 A | * | 8/1996 | Shouse et al. | 34/104 |
| 5,885,263 A | | 3/1999 | Gancet et al. | |
| 5,930,013 A | * | 7/1999 | Fatehi et al. | 398/45 |
| 6,378,224 B1 | * | 4/2002 | Qualkinbush et al. | 34/80 |
| 6,675,421 B1 | * | 1/2004 | Hsu | 12/129.4 |

FOREIGN PATENT DOCUMENTS

| | | | |
|---|---|---|---|
| EP | 0832686 A | | 4/1998 |
| EP | 1157672 A | | 11/2001 |
| JP | 61-216715 | * | 9/1986 |
| WO | WO 91/11977 | | 8/1991 |
| WO | WO 01/52912 | | 7/2001 |

OTHER PUBLICATIONS

International Preliminary Examination Report dated May 6, 2004 for Application No. PCT/GB03/00352.
International Search Report dated May 19, 2003 for Application No. PCT/GB03/00352.
Combined Search and Examination Report dated Jul. 25, 2002 for Application No. GB 0202059.2.
WPI abstract accession No. 1996-459613 [46] & JP 8229343 A (Karushide) Oct. 9, 1996 (see abstract).
WPI abstract accession No. 1990-323513 [43] & JP 2229522 A (Haamo) Dec. 9, 1990 (see abstract).
WPI abstract accession No. 1986-084809 [13] & JP 61031162 A (Matshushita) Jul. 24, 1984 (see abstract).
WPI abstract accession No. 1984-309345 [50] & JP 59193133 A (Kaken Pharma) Jan. 11, 1984 (see abstract).
Database WPI; Section Ch, Week 198645; Derwent Publications Ltd., London, GB; AN 1986-295021; XP002241652 & JP 61 216715 A (Shin Nisso Kako Co Ltd), Sep. 26, 1986; abstract.
Database WPI; Section Ch, Week 199339; Derwent Publications Ltd., London, GB; AN 1993-308422; XP002241653 & JP 05 220327 A (Dai-Ichi Technos KK), Aug. 31, 1993; abstract.
Database WPI; Section Ch, Week 198548; Derwent Publications Ltd., London, GB; AN 1985-299486; XP002241654 & JP 60 206425 A (Enklar Business KK), Oct. 18, 1985; abstract.
Database WPI; Section Ch, Week 199601; Derwent Publications Ltd., London, GB; AN 1996-008643; XP002241655 & KR 9 402 336 B (Hong C), Mar. 23, 1994; abstract.
Database WPI; Section Ch, Week 199028; Derwent Publications Ltd., London, GB; AN 1990-213833; XP002241656 & JP 02 144121 A (Shin Tohoku Kogyo), Jun. 1, 1990; abstract.

* cited by examiner

*Primary Examiner*—S. Gravini
(74) *Attorney, Agent, or Firm*—Norris McLaughlin & Marcus PA

(57) ABSTRACT

The invention relates to a method of absorbing water vapor and malodor from a cavity, for example a drawer or wardrobe or the inside of a shoe. This is achieved by placement in the cavity of a package permeable to water vapor and retaining a particulate dehumidifying compound, a particulate odor-combating compound, and a filler comprising starch or a starch derivative or cellulose or a cellulose derivative, or which acts as a thickener or gelling agent for the water inside the package.

15 Claims, No Drawings

CHEMICAL COMPOSITIONS AND METHODS FOR ABSORBING WATER VAPOR AND COMBATING MALODOR WITHIN A CAVITY

This invention relates to the use of dehumidifying compositions in absorbing water vapour and malodour from the interior of cavities, for example wardrobes, cupboards, drawers and shoes.

It is known to provide odour absorbing and/or sterilizing compositions for use in combating odour produced by domestic waste and by bodily fluids. In particular, domestic waste placed in bins and waste receptacles can generate significant malodour if left for any period of time, especially when the waste is organic such as food and beverage waste. Part of the malodour may be formed by gaseous compounds released from the waste material, and part of the malodour may be formed by volatile compounds within moisture present in the waste material.

Various odour controlling agents have been disclosed in the literature. Many odour-control materials have been described for use with sanitary articles such as nappies and feminine hygiene bins. U.S. Pat. No. 5,885,263 discloses compositions comprising super absorbent polymers containing boron species, which absorb moisture from waste material in the vicinity of the odour controlling composition. WO 01/52912 discloses absorbent articles, such as sanitary napkins, panty liners and nappies comprising lactic acid producing micro-organisms and odour controlling zeolite compounds which absorb malodours from waste material. WO 91/11977 discloses the use of zeolites having intermediate $SiO_2/AlO_2$ ratios to control odours in sanitary articles such as nappies and panty liners.

The odour-control compositions disclosed in the prior art discussed hereinabove comprise a malodour absorbing agent in conjunction with a moisture absorbing agent of a type which absorbs water from moist material with which it is in contact.

It would be advantageous to provide a composition which absorbs malodour and water vapour, from a cavity.

According to a first aspect of the present invention there is provided a method of absorbing water vapour and of combating malodour within a cavity, the method comprising the step of introducing into the cavity a package comprising a wall material which retains particulate contents and is permeable to water vapour, the contents comprising a dehumidifying compound, an odour-combating compound and a filler comprising starch or a starch derivative or cellulose or a cellulose derivative.

According to a second aspect of the present invention there is provided a method of absorbing water vapour and of combating malodour within a cavity, the method comprising the step of introducing into the cavity a package comprising a wall material which retains particulate contents and is permeable to water vapour, the contents comprising a dehumidifying compound, an odour-combating compound, and a filler which acts as a thickener or gelling agent for the water inside the package.

The term "contents" is used throughout this specification to denote the mixture of the dehumidifying compound and the odour-combating compound, and any other materials, mixed therewith, within the package.

Suitably the dehumidifying compound is capable of absorbing at least its own weight of water vapour. Preferably it is capable of absorbing at least twice its own weight of water vapour. The package is preferably manufactured with the dehumidifying compound in a desiccated condition. Preferably the package is kept in a dry environment between manufacture and sale. For example it may be wrapped in a wrapping which is impermeable to water vapour.

The dehumidifying compound is preferably a compound with a high capacity to absorb water vapour. Its capacity to absorb standing water and water entrained in waste materials is not of significance, in this invention.

Preferably the dehumidifying compound comprises an inorganic compound, for example calcium chloride and/or magnesium chloride. When calcium chloride is employed it preferably comprises less than 20 wt % of the total contents. A preferred further dehumidifying compound, additional to calcium chloride, when needed, is magnesium chloride.

Suitably the dehumidifying compound is present in an amount of at least 10 wt %, preferably at least 20 wt %, and mast preferably at least 40 wt %, of the weight of the dry (total) contents. Suitably the dehumidifying compound is present in an amount of no more than 95 wt %, preferably not more than 85 wt % and most preferably not more than 75 wt %, of the weight of the dry (total) contents.

The term "odour-combating" in this specification refers to any manner in which odour is counteracted by way of a physical or chemical action, for example by absorption, suppression, neutralisation or degradation; not merely odour-masking, as a fragrance alone may achieve.

Suitable odour-combating compounds include zeolites, inorganic carbonates, clays, for example bentonite, cyclodextrins and diatomaceous earths.

Suitably the odour-combating compound is present in an amount of at least 0.1 wt % of the weight of the dry (total) contents, more preferably at least 0.5 wt %, most preferably is at least 1 wt %. Suitably the odour-combating compound is present in an amount of no more that 25 wt %, preferably no more than 20 wt %, and most preferably no more than 10 wt % of the weight of the dry (total) contents.

Preferably the odour-combating compound is a zeolite, most preferably comprised within a flowable zeolitic powder.

Preferably a flowable zeolitic powder comprises at least 80 wt % zeolite, and preferably at least 90 wt % zeolite. It may in certain useful embodiments be constituted substantially entirely by zeolite. When it is not, it may be zeolite admixed with a filler or, preferably, processing aid.

In this specification references to "zeolite" are to substantially virgin zeolite, including bound water of crystallisation and any atmospherically absorbed unbound water that may be present, but not including deliberately added materials. "Zeolitic powder" denotes zeolite (as just defined) and also such a material containing deliberately added material(s).

Definitions which refer to the weight or weight ratio of zeolitic powder are made with reference to the zeolite (as defined above) in the zeolitic powder, unless otherwise stated.

We believe that the invention can be applied using any type of odour-absorbing zeolite or zeolitic powder, including odour-absorbing grades of the materials known as zeolite MAP, zeolite X, zeolite P and, most preferably zeolite A.

Suitably, the contents comprise a filler (additional to any starch, starch derivative, cellulose or cellulose derivative filler).

By "filler" we mean a compound which serves to increase the bulk of the composition and which, preferably, is substantially water insoluble. It may however have other functions—for example it may be a processing aid, and/or an odour-absorber and/or have water-absorbing properties and/or act as a thickener or gelling agent for the water absorbed within the package.

A filler may be an inorganic filler, for example a metal salt or metal oxide.

A filler may be an organic filler, for example a compound in the cellulose or starch families (as mentioned above in defining the first aspect of the invention).

Suitable fillers include, for example, calcium carbonate, sodium bicarbonate, cellulose or cellulose derivatives, starch or starch derivatives, anhydrous calcium sulphate, calcium oxide, silica gel, and bentonite clays.

An especially preferred inorganic filler is one selected from the alkaline compounds able to neutralise foot acids, such as the Group IA and Group IIA carbonates and bicarbonates, for example, sodium bicarbonate, potassium bicarbonate, calcium carbonate and magnesium carbonate. Sodium bicarbonate is especially preferred.

An especially preferred organic filler is starch.

Suitably a filler (made up of one or more compounds) is present in an amount of at least 10 wt %, preferably at least 20 wt %, of the weight of the dry (total) contents.

Suitably a filler (made up of one or more compounds) is present in an amount of no more than 80 wt %, preferably no more than 60 wt %, more preferably no more than 40 wt %, of the weight of the dry (total) contents.

As noted above some compounds which are primarily present as a filler may have odour-combating properties. Suitable fillers which have odour-combating properties include inorganic carbonates such as calcium carbonate, clays such as bentonite clays and silica gel.

However, preferred compositions comprise both a highly effective odour-combating compound and a separate filler which may or may not also absorb some odour.

According to this invention a filler which comprises starch or cellulose or a derivative thereof, or a filler which acts as a thickening or gelling agent, is an essential feature. Beyond that, even though some fillers also have some odour-combating properties (or other beneficial secondary properties), in this invention a filler is used in conjunction with a separate odour-combating compound, and is intended primarily as a bulking material, and thus is not an "odour-combating compound" according to the invention.

Preferred contents of the invention comprise a compound capable of absorbing at least its own weight of moisture, especially a magnesium or calcium halide, a filler, especially starch, and an odour-combating compound, especially a zeolite.

The contents may further comprise a fragrance; Many suitable fragrances are commercially available, including those designed to mask waste odours, and the choice of fragrance is a matter of subjective choice. If wished a fragrance may be entrained on an absorbent material, for example on a zeolite employed as an odour-absorbing compound, in order to give slow fragrance release.

The contents may suitably be in the form of a powder, or, preferably, granules (including flakes).

The cavity mentioned above may be an enclosed cavity, for example a drawer, wardrobe, cupboard, locker, refrigerator, freezer, cool box, car boot or car passenger compartment. Preferably it is a drawer, wardrobe, cupboard or locker.

The cavity may be a non-enclosed cavity, for example the inside of a shoe or boot.

In the method the package is placed inside the cavity and, if the cavity has a closure, it is typically closed. The package acts to reduce the humidity of the air inside the cavity and prevent the development of musty odours.

The package may have a wall material which is all of semi-permeable (by which we mean permeable to water vapour and impermeable to water, that is, liquid water) membrane material or may comprise a portion which is wholly water-impermeable membrane and a portion which is of semi-permeable membrane material.

In one convenient embodiment the package comprises a sachet made up of two sheets joined together around their periphery, for example by heat sealing. Preferably one sheet is of a wholly water-impermeable membrane and the other sheet is of a semi-permeable membrane material.

Suitable technology for the package manufacture is described in U.S. Pat. Nos. 6,217,701 and 5,935,304.

Preferably the package is such that it can admit at least 500 g, more preferably at least 1000 g, most preferably at least 2000 g water vapour/$m^2$/day.

The package may have a means for indicating exhaustion. For example the contents may include a component whose colour changes when the water held by the contents reaches a certain level, indicative of exhaustion or imminent exhaustion. Alternatively the package may be designed to bulge visibly when replacement is needed (whilst being designed to be safe from bursting) or otherwise to be detectable by feel, the contents becoming gel-like when approaching exhaustion. Alternatively the package may be formulated such when replacement is required water is no longer all retained by the contents but some drips therefrom, and collects in a visible, distinct under-zone of the package. In that under-zone it may dissolve a colorant, to aid visual detection, or trigger another type of signal, for example a visible or audible signal.

In accordance with a further aspect of the present invention there is provided a package comprising a wall material which retains particulate contents and is permeable to water vapour, the contents comprising a dehumidifying compound, an odour-combating compound, and a filler comprising starch or a starch derivative or cellulose or a cellulose derivative in admixture.

Alternatively, and according to a further aspect of the present invention there is provided a package comprising a wall material which retains particulate contents and is permeable to water vapour, the contents comprising a dehumidifying compound, an odour-combating compound, and a filler which acts as a thickener or gelling agent for the water inside the package, in admixture.

The package is suitably in the form of a pouch or sachet. For certain embodiments it may be provided with a hook, for hanging within the cavity.

In accordance with a further aspect of the present invention there is provided a particulate composition comprising a dehumidifying compound, an odour-combating compound, and a filler comprising starch or a starch derivative or cellulose or a cellulose derivative, in admixture.

Alternatively, and in accordance with a further aspect of the present invention there is provided a particulate composition comprising a dehumidifying compound, an odour-combating compound, and a filler which acts as a thickener or gelling agent for the water inside the package, in admixture.

The invention will now be described by way of the following, non-limiting examples.

EXAMPLE 1

In this example the contents of a sachet to be hung in a wardrobe were as follows:

| | |
|---|---|
| Magnesium chloride in flake form (staple source) | 51 wt % |
| Calcium chloride in flake form (Tokuyama) | 18 wt % |
| Potato starch in powder form (Nichiden Chemical) | 24.9 wt % |
| ZEOCROS E100 (zeolite, Ineos Silicas) | 5 wt % |
| ACTICIDE NC preservative (Thor Specialties) | 0.1 wt % |
| Microencapsulated fragrance | 1.0 wt % |

These materials were mixed in a tumbler mixer. 55 g portions were sandwiched between two rectangular sheets of plastics materials, heat sealed together around their edges, one sheet being polyethylene impermeable to water and water vapour and the other being of semi-permeable TYVEK membrane material from Du Pont, formed from fine HDPE fibres. The water-vapour permeability in this embodiment is about 2000–4000 g/m$^2$/day.

A plastics hook was adhered to the package to enable it to be hung inside a wardrobe.

When the sachet approaches saturation the contents become gel-like. This condition is easy to detect manually.

In a similar example 27 g portions of the same material were employed, between smaller sheets of the same plastics is materials. These smaller packages are for use in drawers.

EXAMPLE 2

In this example the contents of a pouch to be placed inside a shoe were as follows:

| | |
|---|---|
| Magnesium chloride in flake form (staple source) | 40 wt % |
| Potato starch in powder form (Nichiden Chemical) | 38.9 wt % |
| Sodium bicarbonate (staple source) | 10 wt % |
| ZEOCROS E100 (zeolite, Ineos Silicas) | 10 wt % |
| ACTICIDE NC (Thor Specialties) | 0.1 wt % |

These materials were mixed in a tumbler mixer. 100 g portions were entrapped between two rectangular sheets of plastics material, heat sealed together around their edges, one sheet being of polypropylene impermeable to liquid water and water vapour and the other being semi-permeable TYVEK membrane material. The water vapour permeability in this embodiment is about 2000–4000 g/m$^2$/day.

In use, the pouch is placed in a shoe which is damp from wear and/or which requires storage. When approaching saturation the contents became gel-like, easily detected by feel.

ZEOCROS E100, ACTICIDE NC and TYVEK are believed to be trade marks.

The invention claimed is:

1. A method of absorbing water vapour and of combating malodour within a cavity, the method comprising the step of introducing into the cavity a package comprising a wall material which retains particulate contents and is permeable to water vapour, the contents comprising a composition selected from:
   (a) a dehumidifying compound, an odour-combating compound, and a filler comprising starch or a starch derivative or cellulose or a cellulose derivative, and,
   (b) a dehumidifying compound, an odour-combating compound, and a filler which acts as a thickener or gelling agent for the water inside the package wherein the cavity is the interior of an article of footwear or a storage space within an article of furniture.

2. A method according to claim 1 wherein the contents further comprise a filler which is an alkaline compound able to neutralise foot acids.

3. A method according to claim 2, wherein said alkaline compound is sodium bicarbonate.

4. A method according to claim 1 wherein the dehumidifying compound is capable of absorbing at least its own weight of moisture.

5. A method according to claim 1 wherein the dehumidifying compound is a water absorbing metal salt or oxide.

6. A method according to claim 5, wherein the dehumidifying compound is selected from calcium chloride and magnesium chloride.

7. A method according to claim 1 wherein the dehumidifying compound is present in an amount of at least 10 wt % of the weight of the dry contents.

8. A method according to claim 1 wherein the dehumidifying compound is present in an amount of no more than 95 wt % of the weight of the dry contents.

9. A method according to claim 1 wherein the odour-combating compound is a zeolite.

10. A method according to claim 1 wherein the odour-combating compound is present in an amount at least 0.5 wt % of the weight of the dry contents.

11. A method according to claim 1 wherein the odour-combating compound is present in an amount of no more than 25 wt % of the weight of the dry contents.

12. A method according to claim 1 wherein the filler comprises starch or a starch derivative.

13. A method according to claim 1 wherein the filler constitutes at least 10 wt % of the weight of the dry contents.

14. A method according to claim 1 wherein the filler constitutes no more than 80 wt % of the weight of the dry contents.

15. A method according to claim 1 wherein the contents further comprise a fragrance.

* * * * *